US012235268B2

(12) United States Patent
LaBaer et al.

(10) Patent No.: US 12,235,268 B2
(45) Date of Patent: Feb. 25, 2025

(54) IDENTIFICATION AND MEDICAL APPLICATIONS OF ANTI-CITRULLINATED-PROTEIN ANTIBODIES IN RHEUMATOID ARTHRITIS

(71) Applicants: ARIZONA BOARD OF REGENTS ON BEHALF OF ARIZONA STATE UNIVERSITY, Scottsdale, AZ (US); BENAROYA RESEARCH INSTITUTE AT VIRGINIA MASON, Seattle, WA (US)

(72) Inventors: Joshua LaBaer, Chandler, AZ (US); Ji Qiu, Chandler, AZ (US); Kailash Karthikeyan, Gilbert, AZ (US); Jane Buckner, Seattle, WA (US); Gerald Nepom, Seattle, WA (US)

(73) Assignees: SCOTTSDALEARIZONA BOARD OF REGENTS ON BEHALF OF ARIZONA STATE UNIVERSITY, Scottsdale, AZ (US); BENAROYA RESEARCH INSTITUTE AT VIRGINIA MASON, Seattle, WA (US)

( * ) Notice: Subject to any disclaimer, the term of this patent is extended or adjusted under 35 U.S.C. 154(b) by 147 days.

(21) Appl. No.: 16/097,791

(22) PCT Filed: Jun. 14, 2017

(86) PCT No.: PCT/US2017/037492
§ 371 (c)(1),
(2) Date: Oct. 30, 2018

(87) PCT Pub. No.: WO2017/218677
PCT Pub. Date: Dec. 21, 2017

(65) Prior Publication Data
US 2020/0386754 A1    Dec. 10, 2020

Related U.S. Application Data

(60) Provisional application No. 62/350,064, filed on Jun. 14, 2016.

(51) Int. Cl.
| G01N 33/53 | (2006.01) |
| G01N 33/564 | (2006.01) |
| G01N 33/68 | (2006.01) |

(52) U.S. Cl.
CPC ....... *G01N 33/564* (2013.01); *G01N 33/6893* (2013.01); *G01N 2440/18* (2013.01); *G01N 2800/102* (2013.01); *G01N 2800/52* (2013.01)

(58) Field of Classification Search
CPC C07K 14/4713; C07K 14/4743; C07K 14/65; C07K 2317/21; C07K 2317/34; C07K 14/52; C07K 14/575; C07K 16/18; C07K 16/22; C07K 16/24; C07K 16/44; C07K 19/00; G01N 33/564; G01N 244/18; G01N 2800/102; G01N 33/6893; G01N 2440/18; G01N 2800/52; C12N 9/22
See application file for complete search history.

(56) References Cited

U.S. PATENT DOCUMENTS

| 9,442,111 | B2 | 9/2016 | Lindsay |
| 9,535,070 | B2 | 1/2017 | Saul |
| 9,857,374 | B2 | 1/2018 | LaBaer |
| 9,938,523 | B2 | 4/2018 | Labaer |
| 10,045,990 | B2 | 8/2018 | Festa |
| 10,351,842 | B2 | 7/2019 | LaBaer |
| 10,648,978 | B2 | 5/2020 | Wang |
| 2007/0292347 | A1* | 12/2007 | Hill ........................ A61P 37/00 424/1.57 |
| 2014/0162902 | A1 | 6/2014 | Labaer |
| 2014/0371091 | A1* | 12/2014 | Wiktor .................... C40B 50/14 506/9 |
| 2015/0362497 | A1 | 12/2015 | Anderson |

(Continued)

FOREIGN PATENT DOCUMENTS

| WO | 9109616 A1 | 7/1991 |
| WO | 2012021887 A2 | 2/2012 |

(Continued)

OTHER PUBLICATIONS

Wang et al (Proteomics Clin. Appl. 2013, 7, 378-383).*
Kamholtz (Proc. Nail. Acad. Sci. USA vol. 83, pp. 4962-4966, Jul. 1986).*
Carnegie (Biochem J. 1971, 123,57-67).*
Karthikeyan et al (Molecular & Cellular Proteomics (2016), 15(7), 2324-2337 | published May 2, 2016.*
Pratesi, F., et al. (2006) Deiminated Epstein-Barr virus nuclear antigen 1 is a target of anticitrullinated protein antibodies in rheumatoid arthritis. Arthritis Rheumatism 54, 733-741.
Pruijn, G. J. (2015) Citrullination and carbamylation in the pathophysiology of rheumatoid arthritis. Front. Immunol. 6, 192.
Ramachandran, N., et al. (2008) Tracking humoral responses using self assembling protein microarrays. Proteomics Clin. Appl. 2, 1518-1527.

(Continued)

Primary Examiner — Carmencita M Belei
(74) Attorney, Agent, or Firm — Quarles & Brady, LLP

(57) ABSTRACT

Compositions and methods for detection of anti-citrullinated protein antibodies (ACPAs) in rheumatoid arthritis (RA) patients. Patient samples known or suspected of containing ACPAs were probed against citrullinated proteins, and antibody responses to 190 citrullinated proteins in 20 RA patients were investigated. Unique antibody reactivity patterns in both clinical anti-cyclic citrullinated peptide assay positive (CCP+) and negative (CCP-) RA patients were observed. At individual antigen levels, six novel antibody/antigen complexes were discovered and validated against specific citrullinated antigens (Myelin Basic Protein (MBP), osteopontin (SPP1), flap endonuclease (FEN1), insulin like growth factor binding protein 6 (IGFBP6), insulin like growth factor I (IGF1) and stanniocalcin-2 (STC2)) in RA patients. Identification of immune-dominant epitope(s) for citrullinated MBP was also performed. The identified biomarkers have high specificity, especially MBP.

7 Claims, 7 Drawing Sheets

Specification includes a Sequence Listing.

(56) References Cited

U.S. PATENT DOCUMENTS

| | | |
|---|---|---|
| 2016/0041159 A1 | 2/2016 | Labaer |
| 2016/0195546 A1 | 7/2016 | LaBaer |
| 2017/0045515 A1 | 2/2017 | Anderson |
| 2017/0115299 A1 | 4/2017 | Saul |
| 2017/0176423 A1 | 6/2017 | Anderson |
| 2017/0363631 A1 | 12/2017 | Labaer |
| 2018/0067117 A1 | 3/2018 | LaBaer |
| 2018/0201923 A1 | 7/2018 | Labaer |
| 2018/0267029 A1 | 9/2018 | Wiktor |
| 2018/0320230 A1 | 11/2018 | LaBaer |
| 2019/0004051 A1 | 1/2019 | Labaer |
| 2019/0062728 A1 | 2/2019 | Labaer |
| 2019/0127778 A1 | 5/2019 | Labaer |
| 2019/0162725 A1 | 5/2019 | Magee |
| 2019/0302122 A1 | 10/2019 | Katchman |
| 2020/0182874 A1 | 6/2020 | LaBaer |
| 2020/0182887 A1 | 6/2020 | LaBaer |

FOREIGN PATENT DOCUMENTS

| | | | | |
|---|---|---|---|---|
| WO | 2013019680 A1 | 2/2013 | | |
| WO | 2013063126 A2 | 5/2013 | | |
| WO | 2013090364 A1 | 6/2013 | | |
| WO | 2014120902 A1 | 8/2014 | | |
| WO | 2014143954 A2 | 9/2014 | | |
| WO | 2014145458 A1 | 9/2014 | | |
| WO | WO2014143954 | * | 9/2014 | ............. G01N 33/53 |
| WO | WO2014160465 | * | 10/2014 | ............... A61K 9/14 |
| WO | 2015148202 A1 | 10/2015 | | |
| WO | 2015167678 A1 | 11/2015 | | |
| WO | 2015167678 A8 | 11/2015 | | |
| WO | 2015175755 A1 | 11/2015 | | |
| WO | 2016094558 A1 | 6/2016 | | |
| WO | 2016141044 A1 | 9/2016 | | |
| WO | 2017048709 A1 | 3/2017 | | |
| WO | 2017075141 A1 | 5/2017 | | |
| WO | 2017075141 A8 | 5/2017 | | |
| WO | 2017123648 A1 | 7/2017 | | |
| WO | 2018013531 A1 | 1/2018 | | |
| WO | 2018013531 A8 | 1/2018 | | |
| WO | 2019136169 A1 | 7/2019 | | |
| WO | 2019241361 A1 | 12/2019 | | |

OTHER PUBLICATIONS

Ramachandran, N., et al. (2008) Next-generation high density self-assembling functional protein arrays. Nat. Methods 5, 535-538.
Ritter, S. Y., et al. (2013) Proteomic analysis of synovial fluid from the osteoarthritic knee: comparison with transcriptome analyses of joint tissues. Arthritis Rheumatism 65, 981-992.
Robinson, W. H., et al. (2002) Autoantigen microarrays for multiplex characterization of autoantibody responses. Nat. Med. 8, 295-301.
Rosenkranz, M. E., et al. (2010) Synovial fluid proteins differentiate between the subtypes of juvenile idiopathic arthritis. Arthritis Rheumatism 62, 1813-1823.
Santiago, M., et al. (2008) A comparison of the frequency of antibodies to cyclic citrullinated peptides using a third generation anti-CCP assay (CCP3) in systemic sclerosis, primary biliary cirrhosis and rheumatoid arthritis. Clin. Rheumatol. 27, 77-83.
Schwenzer, A., et al. (2015) Identification of an immunodominant peptide from citrullinated tenascin-C as a major target for autoantibodies in rheumatoid arthritis. Anna. Rheumatic Dis. 0, 1-8.
Sinz, A., et al. (2002) Mass spectrometric proteome analyses of synovial fluids and plasmas from patients suffering from rheumatoid arthritis and comparison to reactive arthritis or osteoarthritis. Electrophoresis 23, 3445-3456.
Sokolove, J., et al. (2012) Autoantibody epitope spreading in the pre-clinical phase predicts progression to rheumatoid arthritis. PloS One 7, e35296.
Stoevesandt, O., et al. (2011) Cell free expression put on the spot: advances in repeatable protein arraying from DNA (DAPA). Nat. Biotechnol. 28, 282-290.

Szekanecz, Z., et al. (2008) Anti-citrullinated protein antibodies in rheumatoid arthritis: as good as it gets? Clin. Rev. Allergy Immunol. 34, 26-31.
Takulapalli, B. R., et al. (2012) High density diffusion-free nanowell arrays. J. Proteome Res. 11, 4382-4391.
Tarp, M. A., et al. (2008) Mucin-type O-glycosylation and its potential use in drug and vaccine development. Biochim. Biophys. Acta 1780, 546-563.
Tarp, M. A., et al. (2007) Identification of a novel cancer specific immunodominant glycopeptide epitope in the MUC1 tandem repeat. Glycobiology 17, 197-209.
Taylor-Papadimitriou, J., et al. (1999) MUC1 and cancer. Biochim. Biophys. Acta 1455, 301-313.
Terao, C., et al. (2011) Myelin basic protein as a novel genetic risk factor in rheumatoid arthritis—a genome-wide study combined with immunological analyses. PloS One 6, e20457.
Uchida, T., et al. (2002) Application of a novel protein biochip technology for detection and identification of rheumatoid arthritis biomarkers in synovial fluid. J. Proteome Res. 1, 495-499.
Van Boekel, M. A., et al. (2002) Autoantibody systems in rheumatoid arthritis: specificity, sensitivity and diagnostic value. Arthritis Res. 4, 87-93.
Van Steendam, K., et al. (2011) The relevance of citrullinated vimentin in the production of antibodies against citrullinated proteins and the pathogenesis of rheumatoid arthritis. Rheumatology 50, 830-837.
Van Venrooij, et al. (2008) Anti-CCP antibody, a marker for the early detection of rheumatoid arthritis. Ann. N.Y. Acad. Sci. 1143, 268-285 Antibodies Against Post-translationally Modified Proteins.
Vossenaar, E. R., et al. (2004) Rheumatoid arthritis specific anti-Sa antibodies target citrullinated vimentin. Arthritis Res. Therapy 6, R142-R150.
Weiler, T., et al. (2007) The identification and characterization of a novel protein, c19orf10, in the synovium. Arthritis Res. Therapy 9, R30.
Wiik, A. S., et al. (2010) All you wanted to know about anti-CCP but were afraid to ask. Autoimmunity Rev. 10, 90-93.
Zaenker, P., et al. (2013) Serologic autoantibodies as diagnostic cancer biomarkers—a review. Cancer Epidemiol. Biomarkers Prevention 22, 2161-2181.
Zhu, H., et al. (2001) Global analysis of protein activities using proteome chips. Science 293, 2101-2105.
U.S. Appl. No. 16/901,863, LaBaer, filed Jun. 15, 2020.
U.S. Appl. No. 16/954,201, LaBaer et a;, filed Jun. 15, 2020.
Ademowo, O. S., et al. "Biomarkers of inflammatory arthritis and proteomics." Genes and Autoimmunity: Intracellular Signaling and Microbiome Contribution. InTech (2013): 237-267.
Alessandri, C., et al. (2004) Decrease of anti-cyclic citrullinated peptide antibodies and rheumatoid factor following anti-TNFalpha therapy (infliximab) in rheumatoid arthritis is associated with clinical improvement. Anna. Rheumatic Dis. 63, 1218-1221.
Anderton, S. M. (2004) Post-translational modifications of self antigens: implications for autoimmunity. Curr. Opinion Immunol. 16, 753-758.
Aotsuka, S., et al. (2005) A retrospective study of the fluctuation in serum levels of anti-cyclic citrullinated peptide antibody in patients with rheumatoid arthritis. Clin. Exp. Rheumatol. 23, 475-481.
Apweiler, R., et al. (1999) On the frequency of protein glycosylation, as deduced from analysis of the SWISS-PROT database. Biochim. Biophys. Acta 1473, 4-8.
Bennett, E. P., et al. (2012) Control of mucin-type O-glycosylation: a classification of the polypeptide GalNAc-transferase gene family. Glycobiology 22, 736-756.
Bian, X., et al. (2015) Immunoproteomic profiling of anti-viral antibodies in new-onset type 1 diabetes using protein arrays. Diabetes 65(1), 285-296.
Bian, X., et al. (2015) Antiviral antibody profiling by high-density protein arrays. Proteomics 15, 2136-2145.
Blixt, O., et al. (2010) A highthroughput O-glycopeptide discovery platform for seromic profiling. J. Proteome Res. 9, 5250-5261.
Brahms, H., et al. (2000) The C-terminal RG dipeptide repeats of the spliceosomal Sm proteins D1 and D3 contain symmetrical dimethylarginines, which form a major B-cell epitope for anti-Sm

(56) References Cited

OTHER PUBLICATIONS autoantibodies. Antibodies Against Post-translationally Modified Proteins J. Biol. Chem. 275, 17122-17129.
Bunai, K., et al. (2005) Effectiveness and limitation of twodimensional gel electrophoresis in bacterial membrane protein proteomics and perspectives. J. Chromatogr. B Analyt Technol Biomed Life Sci 815, 227-236.
Burford, B., et al. (2013) Autoantibodies to MUC1 glycopeptides cannot be used as a screening assay for early detection of breast, ovarian, lung or pancreatic cancer. Br. J. Cancer 108, 2045-2055.
Cano, L., et al. (2009) Targeted Synovial Fluid Proteomics for Biomarker Discovery in Rheumatoid Arthritis. Clin. Proteom. 5, 75-102.
Cantaert, T., et al. (2006) Citrullinated proteins in rheumatoid arthritis: crucial.but not sufficient! Arthritis Rheumatism 54, 3381-3389.
Chang, X., et al. (2009) Identification of proteins with increased expression in rheumatoid arthritis synovial tissues. J. Rheumatol. 36, 872-880.
Demoruelle, M. K., et al. (2011) Antibodies to citrullinated protein antigens (ACPAs): clinical and pathophysiologic significance. Curr. Rheumatol. Reports 13, 421-430.
Dieterich, W., et al. (1997) Identification of tissue transglutaminase as the autoantigen of celiac disease. Nat. Med. 3, 797-801.
Fernandes-Cerqueira, C., et al. (2015) Targeting of anti-citrullinated protein/peptide antibodies in rheumatoid arthritis using peptides mimicking endogenously citrullinated fibrinogen antigens. Arthritis Res. Therapy 17, 155.
Forslind, K., et al. (2004) Prediction of radiological outcome in early rheumatoid arthritis in clinical practice: role of antibodies to citrullinated peptides (anti-CCP). Anna. Rheumatic Dis. 63, 1090-1095.
Gobezie, R., et al. (2007) High abundance synovial fluid proteome: distinct profiles in health and osteoarthritis. Arthritis Res. Therapy 9, R36.
Goldman, K., et al. (2013) Anti-citrullinated peptide antibodies is more than an accurate tool for diagnosis of rheumatoid arthritis. Isr. Med. Assoc. J. 15, 516-519.
Gonzalez-Gonzalez, M., et al. (2012) Nanotechniques in proteomics: protein microarrays and novel detection platforms. Eur. J. Pharm. Sci. 45, 499-506.
Gravallese, E. M. (2003) Osteopontin: a bridge between bone and the immune system. J. Clin. Invest. 112, 147-149.
Hagiwara, T., et al. (2002) Deimination of arginine residues in nucleophosmin/B23 and histones in HL-60 granulocytes. Biochem. Biophys. Res. Commun. 290, 979-983.
He, M., et al. (2008) Printing protein arrays from DNA arrays. Nat. Methods 5, 175-177.
Hill, J. A., et al. (2006) Serum autoantibodies that bind citrullinated fibrinogen are frequently found in patients with rheumatoid arthritis. J. Rheumatol. 33, 2115-2119.
Hueber, W., et al. (2005) Antigen microarray profiling of autoantibodies in rheumatoid arthritis. Arthritis Rheumatism 52, 2645-2655.
International Searching Authority, International Search Report and Written Opinion for application PCT/US2017/037492, mailing date of Dec. 1, 2017.
Jenkins, R. E., et al. (2001) Arrays for protein expression profiling: towards a viable alternative to two-dimensional gel electrophoresis? Proteomics 1, 13-29.
Karthikeyan, K., et al. "A contra capture protein array platform for studying post-translationally modified (PTM) auto-antigenomes." Molecular & Cellular Proteomics 15.7 (May 2, 2016): 2324-2337.
Kidd, B. A., et al. (2008) Epitope spreading to citrullinated antigens in mouse models of autoimmune arthritis and demyelination. Arthritis Res. Therapy 10, R119.

Kinloch, A., et al. (2005) Identification of citrullinated alpha-enolase as a candidate autoantigen in rheumatoid arthritis. Arthritis Res. Therapy 7, R1421-R1429.
Klareskog, L., et al. (2008) Immunity to citrullinated proteins in rheumatoid arthritis. Annu. Revi. Immunol. 26, 651-675.
Kokkonen, H., et al. (2011) Antibodies of IgG, IgA and IgM isotypes against cyclic citrullinated peptide precede the development of rheumatoid arthritis. Arthritis Res. Therapy 13, R13.
Kong, Y., et al. (2015) Probing polypeptide GalNActransferase isoform substrate specificities by in vitro analysis. Glycobiology 25, 55-65.
Kuhn, K. A., et al. (2006) Antibodies against citrullinated proteins enhance tissue injury in experimental autoimmune arthritis. J. Clin. Investig. 116, 961-973.
Liao, H., et al. (2004) Use of mass spectrometry to identify protein biomarkers of disease severity in the synovial fluid and serum of patients with rheumatoid arthritis. Arthritis Rheumatism 50, 3792-3803.
Liao, W., et al. (2013) Proteomic analysis of synovial fluid: insight into the pathogenesis of knee osteoarthritis. Int. Orthopaed. 37, 1045-1053.
Low, J. M., et al. (2009) Proteomic analysis of circulating immune complexes in juvenile idiopathic arthritis reveals disease-associated proteins. Proteomics Clin. Appl. 3, 829-840.
Lundberg, K., et al. (2013) Genetic and environmental determinants for disease risk in subsets of rheumatoid arthritis defined by the anticitrullinated protein/peptide antibody fine specificity profile. Anna. Rheumatic Dis. 72, 652-658.
Lutteri, L., et al. (2007) Comparison of second and third-generation anti-cyclic citrullinated peptide antibodies assays for detecting rheumatoid arthritis. Clin. Chim. Acta 386, 76-81.
Macbeath, G., et al. (2000) Printing proteins as microarrays for high-throughput function determination. Science 289, 1760-1763.
Masson-Bessiere, C., et al. (2001) The major synovial targets of the rheumatoid arthritis-specific antifilaggrin autoantibodies are deiminated forms of the alpha- and beta-chains of fibrin. J. Immunol. 166, 4177-4184.
Matsuo, K., et al. (2006) Identification of novel citrullinated autoantigens of synovium in rheumatoid arthritis using a proteomic approach. Arthritis Res. Therapy 8, R175.
Menard, H. A., et al. (2000) Insights into rheumatoid arthritis derived from the Sa immune system. Arthritis Res. 2, 429-432.
Nand, A., et al. (2012) Emerging technology of in situ cell free expression protein microarrays. Protein Cell 3, 84-88.
Nielen, M. M., et al. (2005) Antibodies to citrullinated human fibrinogen (ACF) have diagnostic and prognostic value in early arthritis. Anna. Rheumatic Dis. 64, 1199-1204.
Ogunniyi, A. O., et al. (2009) Screening individual hybridomas by microengraving to discover monoclonal antibodies. Nat. Protocols 4, 767-782.
Park, J., et al. (2006) Recombinational cloning. Curr. Protoc. Mol. Biol., John Wiley & Sons, Inc.
Pedersen, J. W., et al. (2011) Seromic profiling of colorectal cancer patients with novel glycopeptide microarray. Int. J. Cancer 128, 1860-1871.
Boylan, K.B., et al., "Repetitive DNA (TGGA) n 5' to the Human Myelin Basic Protein Gene: A New Form of Oligonucleotide Repetitive Sequence Showing Length Polymorphism," Departments of Neurology and Biochemistry and Biophysics, Division of Medical Genetics, University of California, California Institute of Technology (Apr. 14, 1989) pp. 16-22.
Mohammed, I.D., "Effect of Penicillamine Therapy on Circulating Immune Complexes in Rheumatoid Arthritis," Ann. Rheum. Dis., 5 pages (Oct. 1, 1976).
Terao, C. et al., "Myelin Basic Protein as a Novel Genetic Risk Factor in Rheumatoid Arthritis—A Genome-Wide Study Combined with Immunological Analyses," PLOS ONE, vol. 6, Issue 6, 10 pp. (Jun. 2011).

\* cited by examiner

IDENTIFICATION AND MEDICAL APPLICATIONS OF ANTI-CITRULLINATED-PROTEIN ANTIBODIES IN RHEUMATOID ARTHRITIS

CROSS-REFERENCE TO RELATED APPLICATION

This application represents the national stage entry of PCT International Application No. PCT/US2017/037492, filed on Jun. 14, 2017, and claims priority to U.S. Provisional Application No. 62/350,064, filed on Jun. 14, 2016, the disclosure of which is incorporated herein by reference.

STATEMENT REGARDING FEDERALLY SPONSORED RESEARCH

This invention was made with government support under R21 AR062220 and R42 GM106704 awarded by the National Institutes of Health. The government has certain rights in the invention.

REFERENCE TO A SEQUENCE LISTING SUBMITTED VIA EFS-WEB

The content of the ASCII text file of the sequence listing named "112624_00872_Sequence Listing_ST25.txt" which is 1.21 kb in size was created on Jun. 14, 2017 and electronically submitted via EFS-Web herewith the application is incorporated herein by reference in its entirety.

FIELD OF THE INVENTION

This disclosure relates to biomarker complexes and detection in the field of rheumatoid arthritis.

BACKGROUND OF THE INVENTION

Citrullination is a post translational modification (PTM) that converts arginine to citrulline catalyzed by peptidyl arginine deiminase (PAD). Anti-citrullinated protein antibodies (ACPA) have been specifically detected in rheumatoid arthritis (RA) patients and show utility in RA risk assessment and diagnosis. ACPA levels parallel with RA disease activity, prognosticate erosive diseases, and serve as a surrogate marker for treatment efficacy. Clinically, ACPA are assayed using cyclic citrullinated peptide (CCP), which measures a generalized reactivity with citrulline containing peptides but does not provide information about reactivity to disease-specific RA antigens.

Rheumatoid arthritis (RA) is a common autoimmune disease affecting 1% of the world population and is characterized by the synovial inflammation and joint destruction. Despite decades of research, the cause for rheumatoid arthritis remains unknown. RA has been observed to be heterogeneous through differences in clinical presentation, and the production of different autoantibodies, such as rheumatoid factor (RF) and ACPA. ACPA have been specifically detected in RA patients. ACPA levels correlate with RA disease activity, prognosticate erosive diseases and serve as a surrogate marker for treatment efficacy. The exact mechanism for ACPA production in RA is not clearly understood because citrullination itself is not RA specific. It has been hypothesized that genetic factors, such as specific risk alleles for HLA class II genes and genes involved in immune regulation, together with external factors, such as smoking and viral infections contribute to the break of the immune tolerance leading to the generation of ACPA.

SUMMARY OF THE INVENTION

Embodiments herein relate to a protein array platform that enables the modification of many proteins in parallel and assesses their immunogenicity without the need to express, purify, and modify proteins individually. Anti-citrullinated protein antibodies (ACPAs) in rheumatoid arthritis (RA) were used as a model modification. We first profiled antibody responses to 190 citrullinated proteins in 20 RA patients using a newly developed modification to nucleic acid programmable protein arrays (NAPPA) to identify candidate RA specific antigens. ELISA assays of promising candidates were performed on 100 RA patients and 50 controls. From protein microarray screening experiments, using a discovery set of 20 patients and 10 controls, 6 antigens showing higher reactivity in RA cases relative to controls were subsequently selected for evaluation in a large sample set (n=150) using enzyme-linked immunosorbance assay (ELISA).

A previously unknown 6-antigen set-Myelin Basic Protein (MBP), osteopontin (SPP1), flap endonuclease (FEN1), insulin like growth factor binding protein 6 (IGFBP6), insulin like growth factor I (IGF1), and stanniocalcin-2 (STC-2)—was identified in cyclic citrullinated peptide positive (CCP+) RA samples with a sensitivity of 82%, 50%, 42%, 56%, 52% and 66% respectively at 95% specificity. Additionally the 6-AAb antigens showed 22%, 12%, 10%, 18%, 12% and 12% sensitivity at 95% specificity for cyclic citrullinated peptide negative (CCP−) samples. Thus, we discovered previously unknown antigen complexes, i.e., AAbs, associated with rheumatoid arthritis, with related embodiments directed to diagnostics and rheumatoid arthritis pathogenesis.

Embodiments herein include identification of immunedominant epitope(s) for citrullinated antigen MBP using a protein array. Epitope mapping of MBP was performed as the prevalence to anti-citrullinated (anti-cit)-MBP (82%) was much higher than the other known or novel citrullinated antigens (40-60%) in our sample set. We have shown the two reactive epitopes on MBP: pattern 1, MBP N144-C176 with the corresponding sequence HGSKYLATASTMDHAR-HGFLPRHRDTGILDSIG (SEQ ID NO. 1) and in pattern 2, response was observed for polypeptides MBP N168-C198, which includes the sequence DTGILDSIGRFFGGDR-GAPKRGSGKVSSEE (SEQ ID NO. 2).

DETAILED DESCRIPTION OF THE INVENTION

Figure 1:
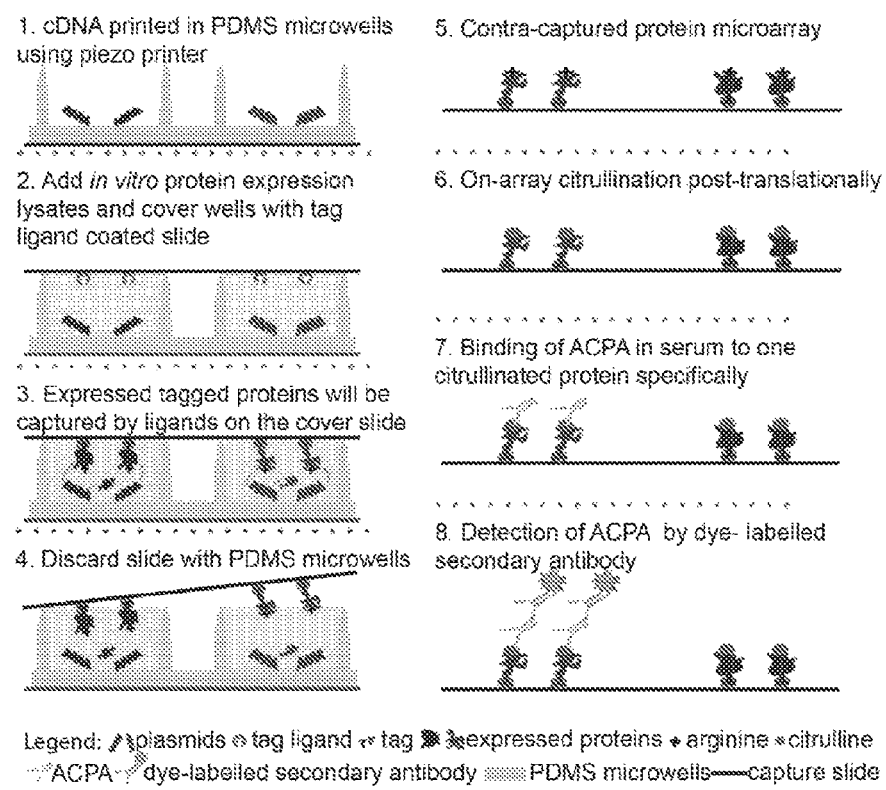
FIG. 1: Principle of the contra capture protein array platform.

Only a few citrullinated antigens have been reported and validated in RA, such as fibrinogen (Fib), enolase-1 (ENO1) and vimentin (VIM). The identification of additional citrullinated antigens and elucidation of their immunodominant epitopes will help develop more sensitive diagnostic assays, and by comparing citrullinated antigens, the assays will achieve higher disease specificity. Therefore, there is a need for identifying more citrullinated antigens to improve performance of current diagnostic tests and also identification of more antigens should help to elucidate the cause of RA.

Citrullinated proteins can trigger host immune responses and elicit antibodies against them in rheumatoid arthritis. The identification of the disclosed autoantibodies (AAbs) and their corresponding antigens impact our knowledge of immunity, leading to early diagnostics and benefiting immunotherapy. Thus, the embodiments herein relate to ACPA's and novel complexes of ACPA's with antigen, as well as their application in diagnostics, research, and treatment.

For example, embodiments herein relate to a composition that includes an in vitro antigen/auto antibody complex associated with rheumatoid arthritis, wherein the complex includes an antigen selected from the group consisting of one or more of Myelin Basic Protein (MBP), osteopontin (SPP1), flap endonuclease (FEN1), insulin like growth factor binding protein 6 (IGFBP6), insulin like growth factor I (IGF1), and stanniocalcin-2 (STC2).

Moreover, embodiments herein relate to a composition that includes an in vitro antigen/auto antibody complex associated with rheumatoid arthritis, wherein the complex includes reactive epitopes of citrullinated MBP selected from the group of MBP N144-C176 (HGSKYLATASTMDHARHGFLPRHRDTGILDSIG) (SEQ ID NO. 1) and MBP N168-C197 (DTGILDSIGRFFGGDRGAPKRGSGKVSSEE) (SEQ ID NO. 2).

Further embodiments relate to a method of detecting rheumatoid arthritis in a patient, including the steps of contacting a patient sample known or suspected to contain antibodies with a substrate including one or more of an antigen selected from the group consisting of Myelin Basic Protein (MBP), osteopontin (SPP1), flap endonuclease (FEN1), insulin like growth factor binding protein 6 (IGFBP6), insulin like growth factor I (IGF1), and stanniocalcin-2 (STC2); and detecting an antibody/antigen complex with one or more of the aforesaid antigens.

Additional embodiments are directed to a method of differentiating rheumatoid arthritis in a patient, including the steps of contacting a patient sample known or suspected to contain antibodies with a substrate including one or more of an antigen selected from the group consisting of Myelin Basic Protein (MBP), osteopontin (SPP1), flap endonuclease (FEN1), insulin like growth factor binding protein 6 (IGFBP6), insulin like growth factor I (IGF1), and stanniocalcin-2 (STC2); and detecting an antibody/antigen complex with one or more of the aforesaid antigens.

Previous studies were mostly performed on western blots using either serum samples or cell lysates followed by separation by either one dimensional (1D) or 2D gel electrophoresis followed by the identification/characterization of reactive protein bands/spots using mass spectrometry. To further confirm the presence of antibodies against a citrullinated protein or a citrullinated epitope on a protein, immunoassays were performed against in vitro citrullinated recombinant proteins using PAD or synthetic peptides with arginine substituted by citrulline.

This approach has proven to be effective, and has the advantage that it examines proteins from natural cell lysates. However, highly abundant proteins in such lysates can obscure the detection of low abundance proteins, identifying the relevant protein in a reactive spot is cumbersome because multiple proteins are often present in the same location, and interpretation of gels can be complicated because multiple isoforms of the same protein may migrate differently. While all these technical challenges can be overcome, the level of effort needed to thoroughly analyze even a single sample prevents this approach from use in large clinical sample sets.

An alternative strategy is the development of high-throughput, unbiased methods to test and identify different candidate antigens in rheumatoid arthritis. Protein microarrays were developed as a method to suit the need of studying antigens in an unbiased high-throughput way.

Embodiments herein are described that relate to high-throughput protein arrays where all proteins are modified simultaneously, probed with samples from rheumatoid arthritis (CCP+, CCP−) and controls to identify citrullinated proteins against which there are antibodies present in samples (FIG. 1). We started with a screen for citrullinated proteins specific antibodies in patients with rheumatoid arthritis using a contra capture nucleic acid programmable protein arrays (NAPPA) displaying 190 full length proteins. Candidate citrullinated proteins were further assessed and validated using a blinded ELISA in an independent set of cases and controls which were age, gender and race matched.

The 6 antigens that we have identified as ones which get citrullinated and have antibodies against them in rheumatoid arthritis with potential of improved sensitivity of current diagnostics assays are (Table 1): MBP, SPP1, FEN1, IGFBP6, IGF1 AND STC2. The identified candidates achieved 86% sensitivity in CCP+ and 22% sensitivity in CCP− at a 95% specificity.

We also used our platform to identify immunodominant epitope(s) for citrullinated antigen MBP. C-terminal deletion mutants for both myelin basic protein (MBP) isoforms were designed based on the following rule: if two arginines were separated by fewer than 9 amino acids, they were treated as a unit; if two arginines were separated by more than 9 amino acids, the amino acids in the middle was used to divide the two arginines into two mutants.

TABLE 1

Discovery and validation statistics of selected candidates.

| Antigen | Sensitivity at 95% specificity | |
|---|---|---|
| | CCP+ (n = 50) | CCP− (n = 50) |
| MBP | 82% | 22% |
| SPP1 | 50% | 12% |
| FEN1 | 42% | 10% |
| IGFBP6 | 56% | 18% |
| IGF1 | 52% | 12% |
| STC2 | 66% | 12% | prehensive picture of ACPA responses in RA. The clinical characteristics of RA are heterogeneous, which may be in part due to the specificity of the immune response directed against post translationally modified antigens. To our knowledge, this is one of the first studies that citrullinated all proteins simultaneously to identify specific citrullinated antigens in a high throughput unbiased way. To ensure accurate estimations of responses when analyzing ELISA results, we also estimated the background associated with the supporting reagent for each plasma sample, which provides the most rigorous assay in similar studies.

Two isoforms of MBP were used for epitope mapping. Isoform 1 (Uniprot: P02686-2) and isoform 2 (Uniprot: P02686-6). We observed two representative immune response patterns to these MBP deletion mutants. In pattern 1, a response was always detected for polypeptides including SEQ ID NO: 1 (MBP T 2.2, FIG. 7). In pattern 2, a response was observed for polypeptides in including SEQ ID NO: 2 (MBP T 2.3, FIG. 7).

In view of the above, one point of novelty is the identification of the 6 autoantigens against which antibodies were detected as candidates in rheumatoid arthritis (Table1). Many of them have not been previously associated with rheumatoid arthritis. In addition, we also were able to identify certain samples as CCP+ which were initially

TABLE 2

Sample information. Descriptive characteristics of samples used to identify and validate AAbs associated with RA

| Characteristics | Discovery | | | Validation | | | p value |
|---|---|---|---|---|---|---|---|
| | CCP+ | CCP− | HC | CCP+ | CCP− | HC | |
| Subjects | 12 | 8 | 10 | 50 | 50 | 50 | 0.87 (one-way ANOVA) |
| Mean age | 60.08 (31-83) | 62.5 (34-89) | 34.1 (22-57) | 52.22 (18-82) | 53.64 (19-89) | 52.54 (19-81) | |
| Sex | | | | | | | |
| Male | 3 | 0 | 4 | 7 | 7 | 7 | 1 (Chi-square test) |
| Female | 9 | 8 | 6 | 43 | 43 | 43 | |
| No data | 0 | 0 | 0 | 0 | 0 | 0 | |
| Race | | | | | | | |
| White | 10 | 8 | 9 | 49 | 48 | 50 | 0.77 (Fisher's exact test) |
| Asian | 2 | 0 | 1 | 0 | 0 | 0 | |
| Indian | 0 | 0 | 0 | 0 | 1 | 0 | |
| other | 0 | 0 | 0 | 1 | 0 | 0 | |
| No data | 0 | 0 | 0 | 0 | 1 | 0 | |

Using an immuno-proteomics approach, we profiled antibody responses against specific citrullinated proteins in CCP+, CCP− rheumatoid arthritis patients. The performance of the candidates identified using protein arrays were confirmed by ELISA using an expanded sample set including subjects from CCP+ (n=50), CCP (n=50), control (n=50) and RA related diseases such as Relapsing Polychondritis (RP) (n=50) and Inflammatory Bowel Disease (IBD) (n=25). Citrullinated MBP was assayed against all 5 serum groups with sensitivities varying from 4% to 82% at 95% specificity. We did not observe significant anti-cit-MBP antibody reactivity in RP and IBD.

The identified candidates highlight the need for identifying more individual antigens in rheumatoid arthritis as it is yet to be understood what causes rheumatoid arthritis. More importantly we believe that the global profiling of ACPAs against antigens in the human proteome and the mapping of their immunodominant epitopes will provide a more comprehensive classified as CCP. Upon rechecking after our analysis the samples initially classified as CCP− using the commercial tests were categorized again as CCP+. Another point of novelty is the method by which the C-terminal mutants for both myelin basic protein were produced and mapping of reactive epitopes in rheumatoid arthritis which has not been done before.

Currently, the diagnostic sensitivities for anti-CCP assay in RA patients range from 68-79% at 86%-95% specificity and there are no high-throughput methods to modify hundreds of protein simultaneously and analyze them. Moreover, the antigens and complexes of antigen with antibody described herein are believed to be novel in the context of rheumatoid arthritis detections and patient differentiation, for example, differentiating RA from osteoarthritis and other conditions.

Non-Limiting Examples

Characteristics of Plasma Samples

A total of 30 serum samples were initially obtained from Benaroya Research Institute, for discovery study. This set consisted of three different groups (CCP+ RA (n=10), CCP− RA (n=10) and Healthy controls (n=10)) were used for the study on protein array and initial testing on ELISA (Table 2). For the validation study a total of 150 samples (CCP+ (n=50), CCP− (n=50) and Healthy controls (n=50)) were obtained and these samples were age, sex and race matched (Table 2).

The patients with rheumatoid arthritis serum samples were obtained from the clinics at the Benaroya Research Institute after receipt of informed patient consent at Benaroya Research Institute under protocols approved by the Institutional Review Board at Arizona State University and Benaroya Research Institute. Regular controls were used in the study and all samples used in the validation study were matched.

In the discovery sample set for protein array experiment, 10 samples per group (CCP+, CCP− and control) were selected. However after experiments two CCP− samples were reclassified as CCP+ and changed the original intended sample numbers per group. For validation purpose, additional 150 patient serum was used with 100 from rheumatoid arthritis patients and 50 controls which were matched.

Protein Array Experiments

Open reading frames were obtained from DNASU (dnasu.org/). All genes of interest were cloned in the nucleic acid-programmable protein array (NAPPA) compatible expression vectors, pJFT7_nHALO or pJFT7_cHALO. Plasmid DNA was prepared and mixed with NAPPA printing buffer prior to printing as previously described. Protein arrays were produced using the following method: plasmid DNA encoding proteins with a HaloTag® comprising a haloalkane dehalogenase are printed in polydimethylsiloxane (PDMS) microwells using a piezoelectric printer. PDMS microwell substrates were blocked with superblock (Thermo Scientific) for 15 minutes at room temperature with gentle rocking and rinsed thoroughly with deionized water. After the application of in vitro protein expression lysates (Human in vitro transcription and translation kit-Thermo Scientific) into the PDMS wells, the wells were covered with a HaloTag® ligand (Promega) coated hydrogel slide (SCHOTT), the ligand comprising a reactive chloroalkane. The hydrogel slide and the PDMS microwell substrate were held together by placing them between the plates of the hybridization chamber DT-1001 (Die-Tech) clamped together using screws from DT-2002 (Die-Tech). The substitution of screws helped us to accommodate the PDMS microwell substrate and capture slide setup (~3.5 mm) better between the hybridization plates. This setup was then placed at 30° C. for 3 hrs and proteins expressed in the wells were covalently immobilized on the HaloTag® ligand coated hydrogel slides through the HaloTag® on each protein. After the capture of expressed proteins, the cover slide are used for subsequent PTM. PTM was followed by blocking with 5% milk in phosphate buffered saline with Tween 20 (milk-PBST), slides were incubated with serum samples (1:300) for 16 h at 4° C., followed by 3 times wash with 5% milk-PBST. Then slides were incubated with Alexa Fluor 647 labeled Goat α Human IgG (Invitrogen) at 23° C. for 1 h. Slides were then washed, dried and scanned by Tecan scanner under consistent settings.

Protein Array Image Analysis and Quantification

Arrays were scanned using Tecan PowerScanner and intensity data were quantified using the ArrayPro image analysis software (MediaCybernetics). Local background subtracted median intensity for replicate spots were used for the analysis. Spots with obvious defects were excluded and corresponding spots from replicate arrays were used for analysis instead. GraphPad Prism software was used for generating jitter plots and un-paired t-test analysis. Heat maps of sample reactivity to proteins were generated using MeV software and a hierarchical cluster analysis using Pearson correlation was performed on the log transformed data.

Candidate Selection

Protein antigens were selected for subsequent ELISA confirmation based on the reactivity that was observed on arrays. The criteria's for selection are: 1) They showed reactivity to serum samples in their citrullinated forms while there was absence of reactivity to their native forms and the same gene was observed for more than 1 sample; 2) If the reactivity was stronger to citrullinated forms of protein compared to the reactivity to native proteins and if the same pattern was observed in more than 1 sample. Totally, 6 protein antigens were selected.

Epitope Mapping

Deletion mutants for myelin basic protein (MBP) isoforms was designed based on the following rule: if two arginines were separated by fewer than 9 amino acids. These rules were designed so that enough numbers of native amino acids surrounding arginines was maintained in our deletion mutants to facilitate their recognition after citrullination by serum antibodies. This also limited the total number of deletion mutants to be assayed for this preliminary study. Based on these rules, primers for each mutant were designed (Integrated DNA Technologies) and mutant genes were PCR amplified and cloned into pJFT7_nHALO expression vector using Gateway recombinational cloning. In total, eight deletion mutants were constructed for each MBP isoforms.

ELISA Assays

ELISA assays were performed to verify selected Ab responses towards citrullinated protein antigens using freshly produced human proteins as previously described. We adapted RAPID ELISA to allow citrullination of target antigen before assessing its sero-reactivity. HaloTag® ligand coated 96 well plates (Promega) were pre-blocked overnight with superblock (Thermo Scientific). Proteins were expressed using hela lysate in vitro transcription-translation system (Thermo Scientific). Protein expression mixture was added into the plates and incubated for 1 hr at room temperature with shaking at 500 RPM to allow the antigen to bind to the HaloTag® ligand in each well. Plates were washed and covalently bound antigens were citrullinated by rmPAD2 at 55° C. for 3 hrs. Citrullinated antigens were incubated with diluted serum samples (1:1000) overnight at 4° C. followed by the addition of Horseradish peroxidase conjugated goat anti human IgG (Jackson Immunoresearch) with shaking at 500 RPM. The plates were developed with the TMB substrate (Thermo Scientific) for 20 minutes and stopped by addition of 2M sulfuric acid. Absorbance at 450 nm was read on Perkin Elmer EnVision Multilabel Reader.

Statistics and Data Analysis

To identify candidates we looked for either: 1) citrullinated protein reactivity to antibodies in the serum compared to no reactivity to their native forms or 2) if reactivity to citrullinated proteins was stronger than reactivity to native proteins in more than one sample.

For all spots identified, local background subtracted median intensity for replicate spots were used for the analysis. Spots with obvious defects were excluded and corresponding spots from replicate arrays were used for analysis instead.

Figure 2:
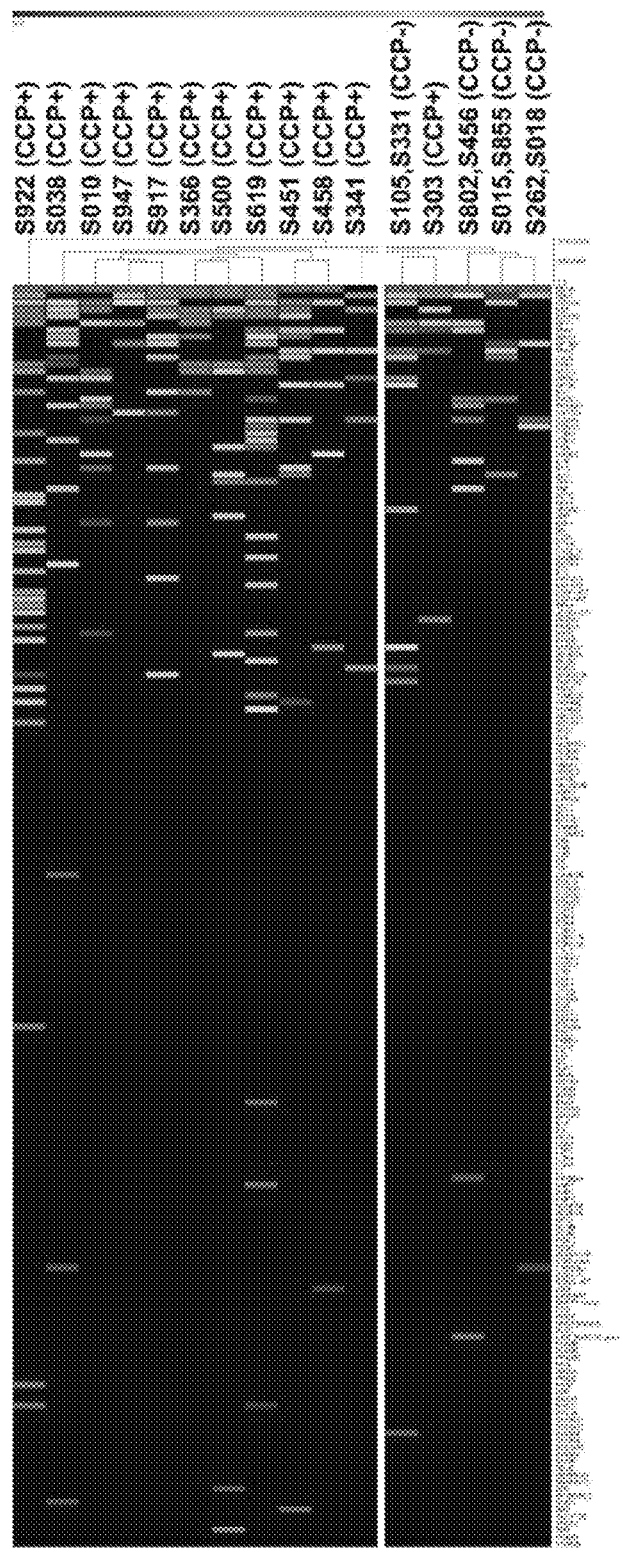
FIG. 2: A. Heat map depicting overall reactivity of 20 CCP+ and CCP− serum samples to 190 genes printed on array. CCP− RA samples were assayed as pools of two samples as annotated on the top of the figure. Blue, low reactivity; red, high reactivity. B. Example array images probed with CCP+RA patient serum samples.
Figure 3:
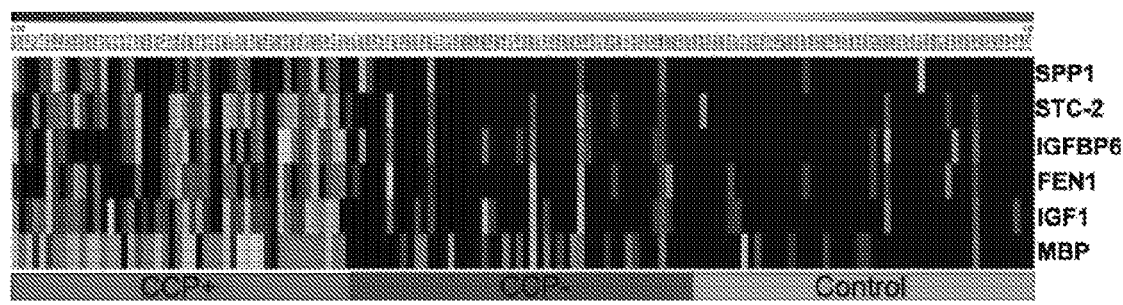
FIG. 3: Assaying 6 novel antigens against validation serums. Heat map depicting sero-reactivity against citrullinated antigens assayed by ELISA in different groups of the independent sample set.

A heatmap was developed to display differential Ab responses of the 30 serums to all 190 citrullinated proteins (FIG. 2). A heatmap was also generated to show the 6 selected targets in 150 rheumatoid arthritis patients and controls using the confirmation ELISA results (FIG. 3). The heatmap color was scaled according to strength of the reactivity.

We categorized subjects as Ab responders from ELISA analysis of each antigen if there was a significant difference between CCP+vs control and CCP+vs CCP−. We performed t-test analysis for the groups to verify differences and validate.

Identification of Candidate Antigens Associated with Rheumatoid Arthritis

Figure 4:
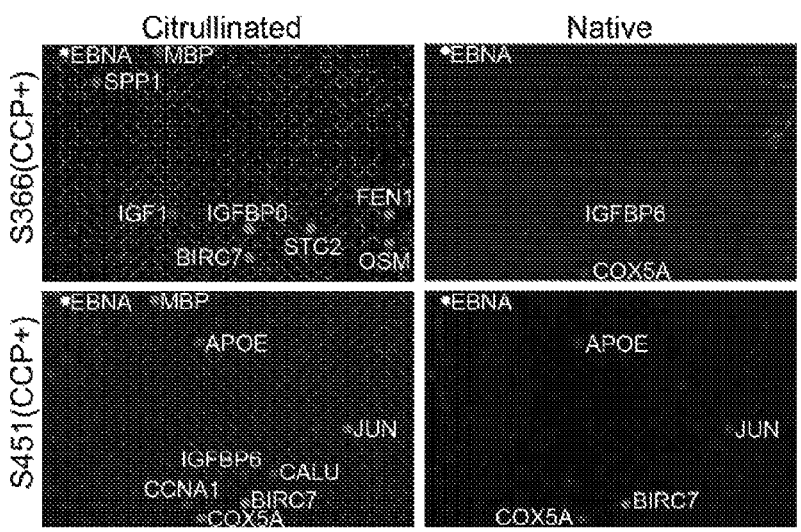
FIG. 4: Sero-profiling of ACPAs in RA patients on contra capture protein arrays against 190 antigens. Example array images probed with CCP+RA patient serum samples (S366 and S451).
Figure 5:
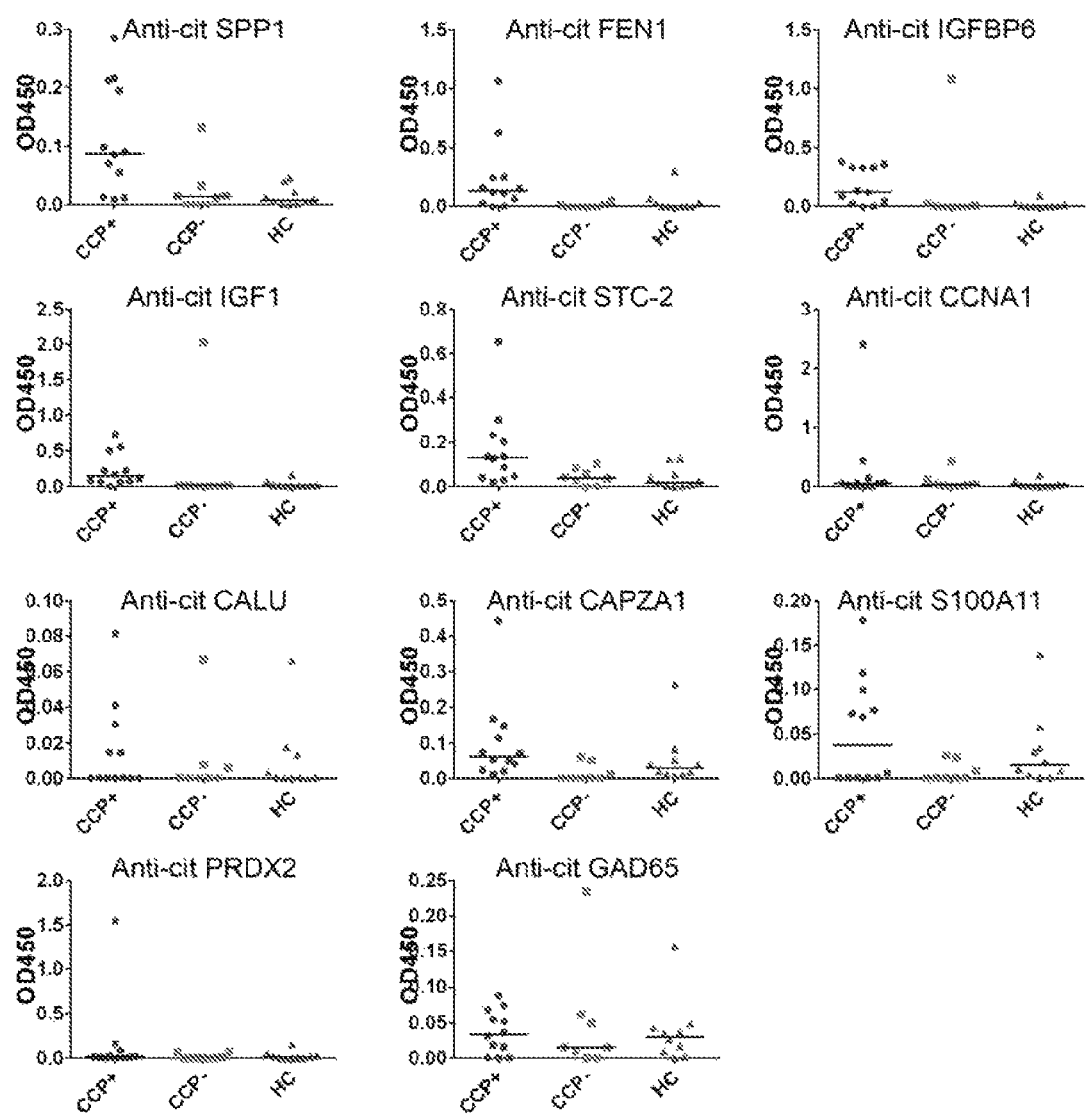
FIG. 5: Analysis and verification of new targets identified on contra capture arrays by ELISA. 11 antigens identified on protein array assayed, by ELISA, against 30 serum samples from discovery set.

To identify rheumatoid arthritis associated candidate Abs, we first performed comprehensive profiling of antibodies against 190 full-length human proteins in serum samples from 20 rheumatoid arthritis and 10 control patients on contra capture NAPPA. Based on the array data, we selected 11 antigens (SPP1, FEN1, IGFBP6, IGF1, STC2, cyclin-A1 (CCNA1), calumenin (CALU), F-actin-capping protein subunit alpha-1 (CAPZA1), protein S100-A11 (S100A11), peroxiredoxin-2 (PRDX2) and glutamate decarboxylase 2 (GAD65)) that showed high antibody reactivity against their citrullinated form in several RA patients and assessed the antibody reactivity of their citrullinated form in all thirty clinical samples by ELISA (FIG. 4 and FIG. 5). Of these, SPP1 is a protein selected based on its high expression in synovial fluid in patients with erosive RA. To our knowledge it is not known whether SPP1 is citrullinated in RA. Antibodies against citrullinated SPP1 showed the best differential reactivity between RA patients and healthy controls.

Validation of Candidate Antigens Associated with Rheumatoid Arthritis

Figure 6:
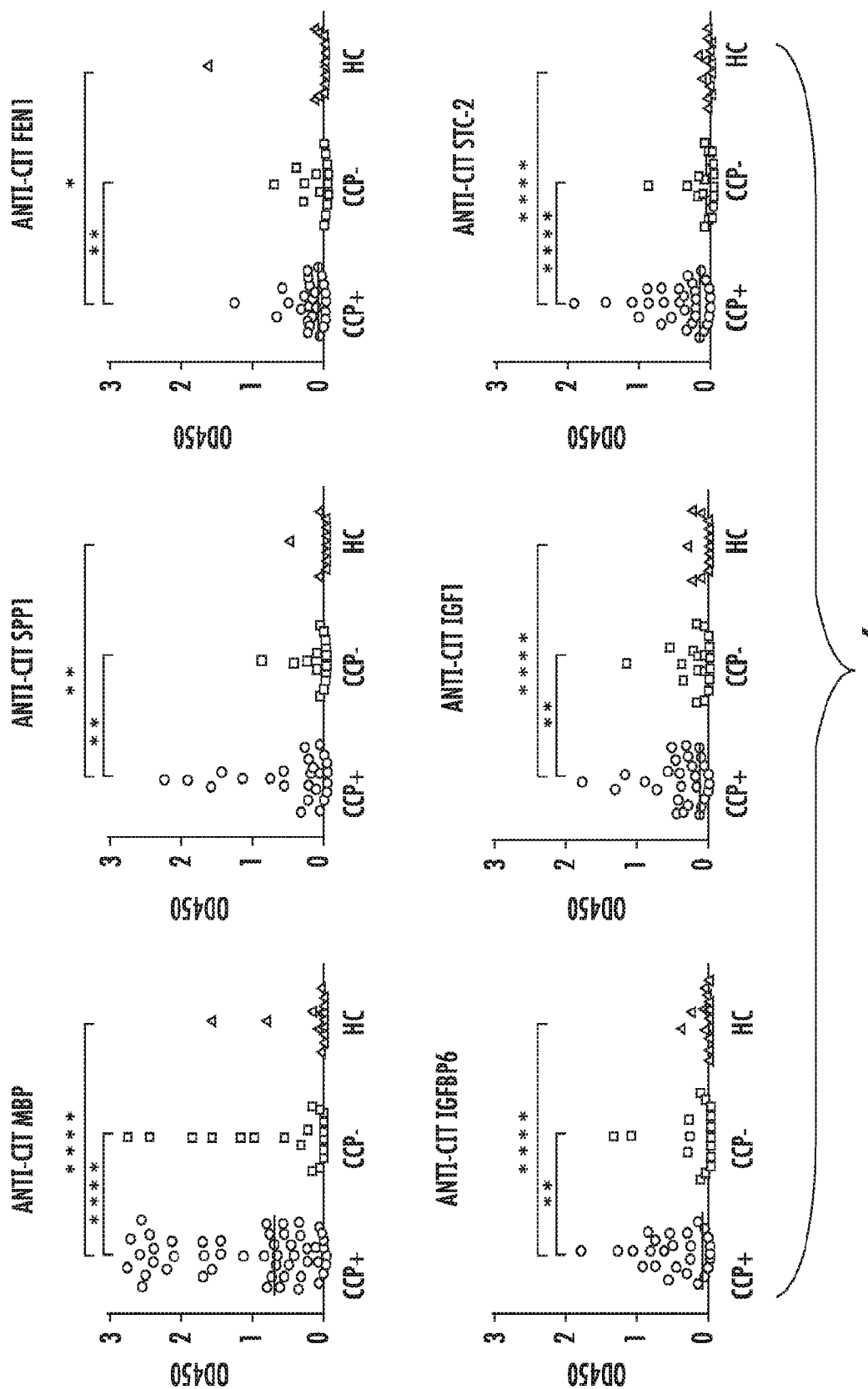
FIG. 6: Validation, by ELISA, of novel ACPAs identified on contra capture arrays. Blinded validation of selected novel ACPAs, by ELISA, using an independent set of 150 sera comprising 50 CCP+, 50 CCP− and 50 control samples. HC, healthy control. * indicates t-test p<0.05, p<0.01 and **p<0.0001.

To validate these novel ACPA, we performed a blinded study of responses in ELISA to SPP1, FEN1, IGFBP6, IGF1 and STC2 in an independent set of 150 serum samples from groups of subjects with three different clinical characteristics: CCP+RA patients (50); CCP− RA patients (50); and healthy controls (50) (Table 2). We observed significant differences for the antigens' reactivity between the CCP+RA and healthy control groups (FIG. 6). At 95% specificity, the sensitivity of predicting RA with the new ACPAs was 50%, 42%, 56%, 52% and 66% in CCP+RA patients for SPP1, FEN1, IGFBP6, IGF1 and STC2, respectively (Table 1). Surprisingly, response levels to these five ACPAs were also higher in a number of CCP− RA patients, who were clinically categorized as not responsive to standard citrullinated antigens. The sensitivities in the CCP− RA patients were 12%, 10%, 18%, 12%, and 12%, respectively (Table 1). We also assayed anti-cit-MBP antibodies in these samples by ELISA. At 95% specificity, the sensitivity for cit-MBP was 82% for CCP+ serum and 22% for CCP− serum samples.

Epitope Mapping

It is often useful to determine which epitopes are recognized by antibodies in an immune response. For epitope mapping, ELISA is usually performed on overlapping peptides. This requires the synthesis of multiple native and modified peptides and is a costly process. Recognizing that our platform can manipulate epitopes at the DNA level, followed by display and citrullination of the peptides expressed in vitro, we performed epitope mapping to identify immune-dominant citrullinated epitopes for MBP in RA.

Epitope mapping of MBP was performed as it is a poorly studied citrullinated antigen for RA. Two isoforms of MBP were used for epitope mapping. Isoform 1 (Uniprot: P02686-2) and isoform 2 (Uniprot: P02686-6). C-terminal serial deletion mutants of these two MBP isoforms were constructed, expressed, citrullinated, and probed with MBP reactive serum samples on arrays.

Figure 7:
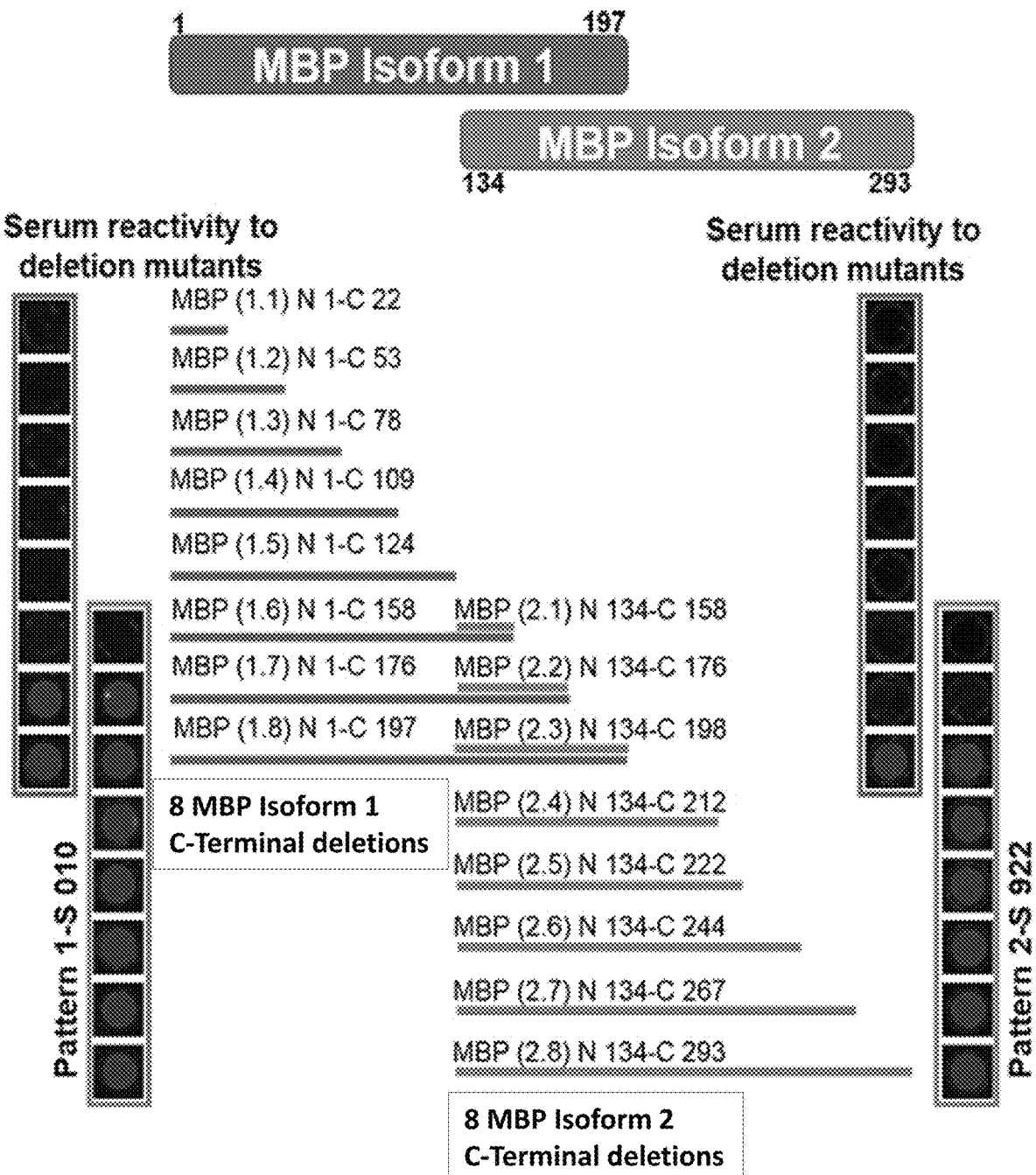
FIG. 7: Epitope mapping for MBP. Eight C-terminal deletion fragments were constructed for each isoform of MBP. Two response patterns were observed. In pattern 1, reactivity to deletion mutants MBP 1.7, MBP 1.8, MBP 2.2 and MBP 2.3 were observed. In pattern 2, reactivity to deletion mutants MBP 1.8 and MBP 2.3 were observed, but not to MBP 1.7 and MBP2.2. MBP 1.7 and MBP 2.2 shared the same sequence and MBP 1.8 and MBP 2.3 shared same sequence. The immunodominant epitopes for the pattern 1 (sample S010) are shown on the left side, and for the pattern 2 (sample S922) on the right side.
Figure 8:
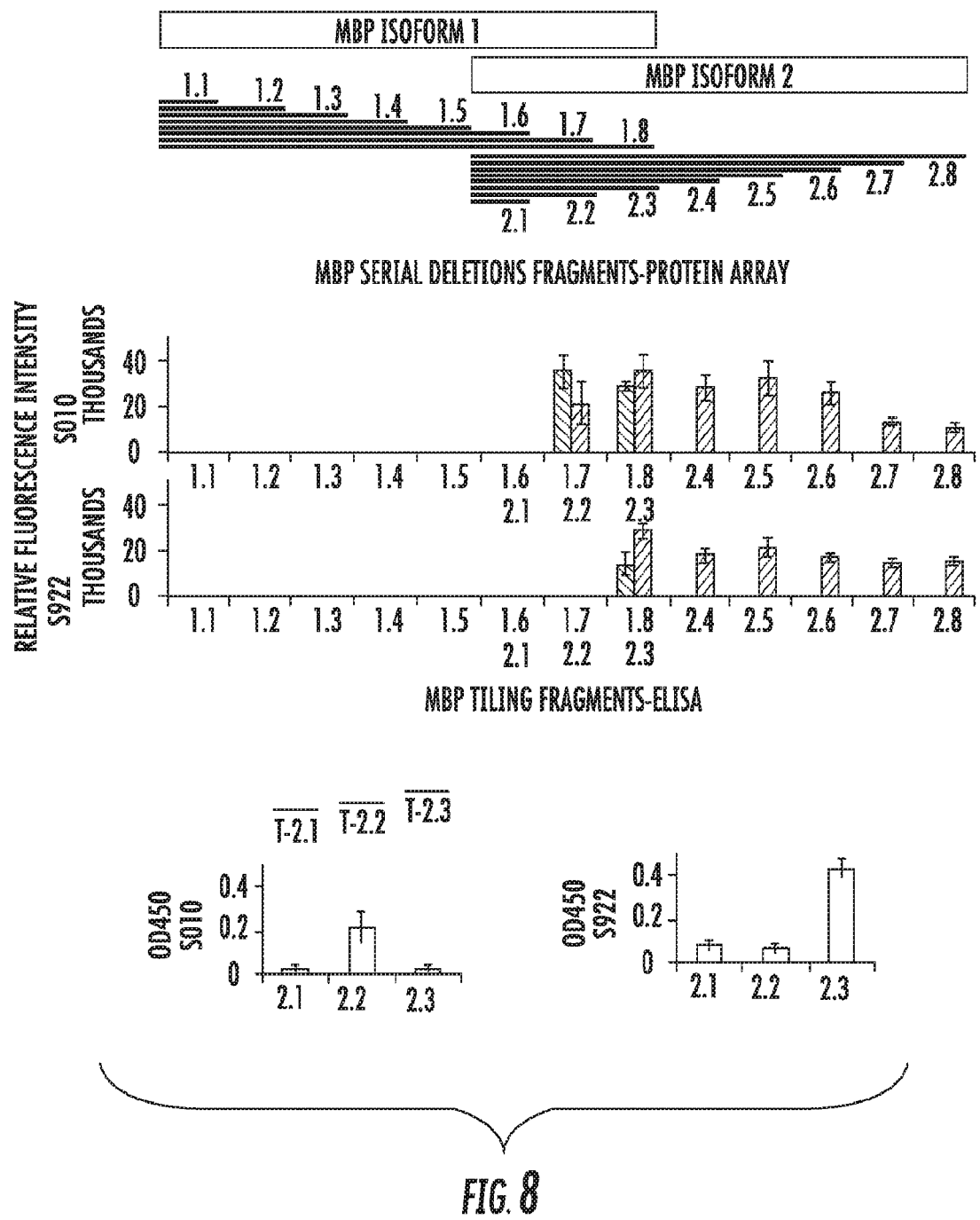
FIG. 8: Epitope mapping, by ELISA, for MBP using serial deletion fragments and tiling fragments. Top, diagram for the two MBP isoforms and serial deletion mutants used in this study. Middle, quantitative analysis of sero-reactivity to the deletion mutants for S922 and S010 serum samples on arrays. Bottom, sero-reactivity to the tiling fragments of the overlapping region of MBP isoform 1 and 2. S922 reacted with T-2.3 and S010 reacted with T2.2. This matched the results on arrays with deletion mutants.

We observed two representative immune response patterns to these MBP deletion mutants. Within each pattern, the reactivity to isoform 1 and isoform 2 deletion mutants was consistent in the overlapping regions (FIG. 7). In pattern 1, a response was always detected for polypeptides including MBP with T 2.2 the corresponding sequence HGSKYLATASTMDHARHGFLPRHRDTGILDSIG (SEQ ID NO. 1) and in pattern 2, response was observed for polypeptides MBP T 2.3, which includes the sequence DTGILDSIGRFFGGDRGAPKRGSGKVSSEE) (SEQ ID NO. 2). To pinpoint the reactive epitope in the region N131-C205, we constructed tiling fragments of MBP T (2.1) N134-C158, T (2.2) N144-C176, T (2.3) N168-C198, and assayed antibody reactivity using all serum samples. We found several serum samples reacting to region MBP N168-C198 and the rest to region MBP N131-C205 (Suppl. FIG. 5 FIG. 8). No reactivity was seen on other deletion mutants of either isoform lacking this sequence. Thus we were able to use this platform to rapidly identify two distinct B cell epitopes in citrullinated MBP.

Using an immuno-proteomics approach, we applied serum samples to arrays displaying hundreds of citrullinated proteins in parallel. We were able to detect specific antibody reactivity to known citrullinated proteins in RA patients. We provided the first glimpse of reactivity patterns of 20 RA patients against ~190 individual citrullinated antigens. We observed two clusters of samples clinically classified as CCP+ and CCP−; additionally, each sample seemed to have its own unique reactivity pattern (FIG. 2).

We discovered and validated six novel ACPAs in RA patients against antigens MBP, SPP1, FEN1, IGFBP6, IGF1 and STC2. Antibodies against citrullinated SPP1 are particularly interesting because SPP1, also known as osteopontin, is a candidate marker elevated in synovial fluid of patients with erosive RA, though it has never been shown to be a citrullinated antigen. We observed immune reactivity specific to citrullinated SPP1 in 50% of CCP+ patients and 12% of CCP− patients at a specificity of 95% in our blinded validation study. SPP1 is recognized as a potential proinflammatory cytokine associated with inflammatory processes. Its discovery as a specific antibody target in RA, from among almost 200 candidates, suggests the possibility of a role that it or the immune response to it might play in the disease.

Anti-cit-MBP has the highest prevalence among the ACPAs that we assayed in this study. Citrullinated MBP has been reported in other diseases such as multiple sclerosis (MS) and other demyelinating diseases and is believed to be involved in the pathogenesis of CNS autoimmune diseases. Here, we detected anti-cit-MBP antibodies in a large fraction of RA patients (~80% of CCP+ samples), which agrees with a previous report on the expression of MBP in the synovial lining and the presence of anti-cit-MBP in RA. In conjunction with the fact that the prevalence to anti-cit-MBP (82%) was much higher than the other known or novel citrullinated antigens (40-60%) in our sample set, it seems likely that these two citrullinated HGSKYLATASTMDHARHGFLPRHRDTGILDSIG (SEQ ID NO. 1) and DTGILDSIG- RFFGGDRGAPKRGSGKVSSEE (SEQ ID NO. 2), may represent novel immunodominant epitopes in RA, whose biological implications warrant further investigations.

We also calculated the sensitivities and specificities of all 6 candidate antigens that went into the validation study. The physiological relevance of these novel ACPAs warrants future investigation. More importantly, we believe that the global profiling of ACPAs against antigens in the human proteome and the mapping of their immunodominant epitopes will provide a more comprehensive picture of ACPA responses in RA. The clinical characteristics of RA are heterogeneous, which may be in part due to the specificity of the immune response directed against post translationally modified antigens.

Assessing reactivity to immune-dominant antigens/epitopes in longitudinal samples collected from high-risk subjects or in patients with different clinical parameters (such as environmental exposures) will promote a better understanding of RA pathogenesis and stratification of RA patients into subtypes based on their response signatures, which based on this initial study may impact the CCP– RA population as it is now defined.

One of the strengths of this study is that protein arrays display many proteins, which make them suitable to screen thousands of proteins against multiple samples for discovery studies. A key expectation is that they will discover new candidate targets which will need to be validated in many more samples. To address the need to test a small number of candidate antigens against many samples (hundreds to thousands), we adapted this method to produce an ELISA assay that supports protein modification and is compatible with biomarker validation/verification studies. This method dovetails with arrays by exploiting the same plasmid clones, without the need to transfer the gene, and it avoids the need to optimize and execute the expression and purification of recombinant proteins as needed by conventional ELISA. We created a system to citrullinate multiple proteins simultaneously and screen them without bias to identify novel antigens in RA. By increasing the number of proteins used for screening, our chances of identifying novel candidates increase accordingly. By performing an unbiased screen we identified MBP where prevalence to anti-cit-MBP (82%) was much higher than the other known and established citrullinated antigens.

To evaluate these Abs' against citrullinated antigens performance, we used more clinically relevant ELISA assays in large sample sets, and performed independent blind validation. Our results were also consistent with results obtained on protein arrays.

In summary, we have developed a platform that can assay sero-reactivity to many post-translationally modified antigens in parallel. We screened 190 proteins, and utilized rmPAD2 to determine reactivity in RA sera to known and novel citrullinated protein epitopes. We observed unique antibody reactivity patterns in both clinical anti-cyclic citrullinated peptide assay positive (CCP+) and negative (CCP–) RA patients.

At individual antigen levels, we detected antibodies against known citrullinated autoantigens and discovered and validated six novel antibodies against specific citrullinated antigens: Myelin Basic Proteins (MBP), osteopontin (SPP1), flap endonuclease (FEN1), insulin like growth factor binding protein 6 (IGFBP6), insulin like growth factor I (IGF1) and stanniocalcin-2 (STC2)) in RA patients. We also identified immune-dominant epitope(s) for citrullinated antigen MBP in RA samples-MBP, HGSKYLATASTMDHAR-HGFLPRHRDTGILDSIG (SEQ ID NO. 1) and DTGILD-SIGRFFGGDRGAPKRGSGKVSSEE (SEQ ID NO. 2).

The following claims are not meant to be limited to the particular embodiments and examples herein.

What is claimed is:

1. A method of detecting anti-citrullinated antibodies in a sample from a rheumatoid arthritis patient, comprising the steps of:
   (i) contacting a plasma or serum sample obtained from the patient with a substrate comprising
      at least one in vitro citrullinated antigen selected from the group consisting of a Myelin Basic Protein (MBP) peptide fragment consisting of the sequence of SEQ ID NO. 1, and an MBP peptide fragment consisting of the sequence of SEQ ID NO. 2 and
      at least one additional in vitro citrullinated antigen selected from the group consisting of osteopontin (SPP1), flap endonuclease (FEN1), insulin like growth factor binding protein 6 (IGFBP6), insulin like growth factor I (IGF1), and stanniocalcin-2 (STC2) to form antibody-antigen complexes; wherein the at least one antigen and the at least one additional antigen are each linked to a haloalkane dehalogenase, wherein the substrate is coated with a ligand comprising a reactive chloroalkane capable of binding the haloalkane dehalogenase, thereby immobilizing the at least one antigen and the at least one additional antigen on the substrate;
   (ii) contacting the antibody-antigen complexes with a label; and
   (iii) detecting the antibody-antigen complexes, thereby detecting the anti-citrullinated antibodies in the sample by detecting the label.

2. The method of claim 1, further comprising treating the patient with a therapeutic agent, and using steps (i)-(iii) to detect a quantity of the antibody-antigen complex to determine if said quantity of the antibody-antigen complex increases, decreases, or remains the same.

3. The method of claim 1, wherein the sample is a serum sample.

4. The method of claim 1, wherein prior to step (i) the method includes:
   (a) depositing into microwells plasmid DNA that encodes the at least one antigen and the at least one additional antigen, wherein the at least one antigen and the at least one additional antigen are each linked to the haloalkane dehalogenase in the plasmid along with in vitro protein expression lysates to allow for the expression of the at least one antigen and the at least one additional antigen, each linked to the haloalkane dehalogenase, in the protein expression lysates;
   (b) contacting the protein expression lysates comprising the expressed at least one antigen and the at least one additional antigen, each linked to the haloalkane dehalogenase, with the substrate coated with the reactive chloroalkane; and
   (c) citrullinating the immobilized at least one antigen and the at least one additional antigen post-translationally on the substrate.

5. The method of claim 1, wherein prior to step (i) the at least one antigen and the at least one additional antigen are citrullinated post-translationally.

6. The method of claim 1, wherein the label is a dye-labeled secondary antibody.

7. The method of claim 6, wherein the dye-labeled secondary antibody is a labeled anti-human IgG.

* * * * *

UNITED STATES PATENT AND TRADEMARK OFFICE
CERTIFICATE OF CORRECTION

| | | |
|---|---|---|
| PATENT NO. | : 12,235,268 B2 | Page 1 of 1 |
| APPLICATION NO. | : 16/097791 | |
| DATED | : February 25, 2025 | |
| INVENTOR(S) | : Joshua LaBaer et al. | |

It is certified that error appears in the above-identified patent and that said Letters Patent is hereby corrected as shown below:

On the Title Page

Item (73) Assignees: "SCOTTSDALEARIZONA BOARD OF REGENTS ON BEHALF OF ARIZONA STATE UNIVERSITY" should be --"ARIZONA BOARD OF REGENTS ON BEHALF OF ARIZONA STATE UNIVERSITY"--.

Signed and Sealed this
Fourteenth Day of October, 2025

John A. Squires
*Director of the United States Patent and Trademark Office*

SEQUENCE LISTING

```
<160> NUMBER OF SEQ ID NOS: 2

<210> SEQ ID NO 1
<211> LENGTH: 33
<212> TYPE: PRT
<213> ORGANISM: Artificial Sequence
<220> FEATURE:
<223> OTHER INFORMATION: In vitro synthesized epitope to citrullinated
      Myelin Basic Protein

<400> SEQUENCE: 1

His Gly Ser Lys Tyr Leu Ala Thr Ala Ser Thr Met Asp His Ala Arg
1               5                   10                  15

His Gly Phe Leu Pro Arg His Arg Asp Thr Gly Ile Leu Asp Ser Ile
            20                  25                  30

Gly

<210> SEQ ID NO 2
<211> LENGTH: 30
<212> TYPE: PRT
<213> ORGANISM: Artificial Sequence
<220> FEATURE:
<223> OTHER INFORMATION: In vitro synthesized epitope to citrullinated
      Myelin Basic Protein
```

-continued

```
<400> SEQUENCE: 2

Asp Thr Gly Ile Leu Asp Ser Ile Gly Arg Phe Phe Gly Gly Asp Arg
1               5                   10                  15

Gly Ala Pro Lys Arg Gly Ser Gly Lys Val Ser Ser Glu Glu
            20                  25                  30
```